United States Patent [19]

Kaiser et al.

[11] Patent Number: 4,572,795
[45] Date of Patent: Feb. 25, 1986

[54] ODORANT SUBSTANCES

[75] Inventors: Roman Kaiser, Uster; Dietmar Lamparsky, Wangen, both of Switzerland

[73] Assignee: Givaudan Corporation, Clifton, N.J.

[21] Appl. No.: 461,054

[22] Filed: Jan. 26, 1983

[30] Foreign Application Priority Data

Jan. 27, 1982 [CH] Switzerland ............... 491/82

[51] Int. Cl.[4] .............. A61K 7/46; C07C 33/03; C07C 33/02
[52] U.S. Cl. ................. 252/522 R; 131/276; 252/174.11; 424/49; 424/65; 424/69; 424/70; 424/76; 568/840
[58] Field of Search .............. 252/522 R; 568/840

[56] References Cited

U.S. PATENT DOCUMENTS

| | | | |
|---|---|---|---|
| 3,781,368 | 12/1973 | Neale | 568/687 X |
| 3,920,752 | 11/1975 | Lamparsky | 260/601 R |
| 4,122,291 | 10/1978 | Kyo et al. | 568/887 |
| 4,168,248 | 9/1979 | Kulka | 252/522 R |
| 4,347,388 | 8/1982 | Gramlich et al. | 252/522 R X |

FOREIGN PATENT DOCUMENTS 0045453 2/1982 European Pat. Off. .

OTHER PUBLICATIONS

Arctander, *Perfume and Flavor Chemicals*, vol. II, Monographs 1960 and 1961, (1969).
Bjelouss, Ber., vol. 43, (1910), 2330–2333.

*Primary Examiner*—Thomas A. Waltz
*Attorney, Agent, or Firm*—Robert F. Tavares

[57] ABSTRACT

The invention is concerned with compounds of the formula:

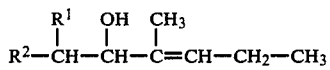

wherein:
$R^1$ is selected from the group consisting of hydrogen and methyl;
$R^2$ is selected from the group consisting of normal or terminally singly branched alkyl or alkenyl groups having four to seven carbon atoms provided that:
(i) when $R^1$ is hydrogen the alkyl group must have at least five carbon atoms, and
(ii) when $R^1$ is methyl, $R^2$ is an alkyl group.

This invention is also concerned with odorant compositions containing these compounds.

21 Claims, No Drawings

ODORANT SUBSTANCES

THE INVENTION

The present invention is concerned with novel compounds of the formula

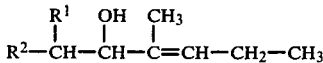

wherein:

$R^1$ is selected from the group consisting of hydrogen and methyl;

$R^2$ is selected from the group consisting of normal or terminally singly branched alkyl or alkenyl groups having four to seven carbon atoms provided that (i) when $R^1$ is hydrogen the alkyl group must have at least five carbon atoms, and (ii) when $R^1$ is methyl, $R^2$ is an alkyl group.

This invention is also concerned with odorant compositions containing these compounds.

By a terminally singly branched alkyl or alkenyl group is meant that the next to the last carbon in an otherwise straight chain has a methyl branch on it, i.e. the chain terminates in either an isopropyl, isopropenyl or an isopropylidene group.

DESCRIPTION OF THE PREFERRED EMBODIMENTS

The normal or terminally singly branched alkyl or alkenyl groups contemplated include n-butyl, iso-butyl, n-amyl, iso-amyl, n-hexyl, iso-hexyl, n-heptyl, iso-heptyl, methallyl, butenyl, methylbutenyl, methylpentenyl, pentenyl, etc. Of the alkenyl groups, those that are terminally branched e.g. methylbutenyl or methylpentenyl are preferred. Of the alkyl groups, the lower homologs are preferred over the higher homologs, e.g. n-amyl and isoamyl when $R^1$ is hydrogen and n-butyl and isobutyl when $R^1$ is methyl.

While $R^1$ may be hydrogen or methyl, those compounds wherein $R^1$ is hydrogen are preferred. Those wherein $R^1$ is hydrogen and $R^2$ is an alkyl group of five to seven carbon atoms are especially preferred.

Among those secondary alcohols which formula I is especially intended to embrace are the following, with the compounds designated by * being the most preferred:

| | |
|---|---|
| 4-methyl-undec-3-en-5-ol | (Ia)* |
| 4-methyl-dodec-3-en-5-ol | (Ib) |
| 4-methyl-tridec-3-en-5-ol | (Ic) |
| 4,6-dimethyl-dec-3-en-5-ol | (Id)* |
| 4,6-dimethyl-undec-3-en-5-ol | (Ie) |
| 4,9-dimethyl-dec-3-en-5-ol | (If)* |
| 4,6,8-trimethyl-non-3-en-5-ol | (Ig)* |
| 2,6-dimethyl-1,6-nonadien-5-ol | (Ih)* |
| 4-methyl-3,9-decadien-5-ol | (Ii) |
| 4-methyl-3,8(Z)-undecadien-5-ol | (Ij) |
| 4,9-dimethyl-3,8-decadien-5-ol | (Ik) |
| 4,10-dimethyl-3,9-undecadien-5-ol | (Il) |

All of the possible stereoisomers are intended to be embraced by formula I including the cis or trans isomers at the double bond.

The invention is also concerned with a process for the manufacture of the compounds of formula I. This comprises reacting 2-methyl-2-pentenal with a halide of the formula

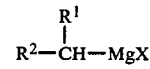

wherein $R^1$ and $R^2$ are as previously defined, and X stands for halogen.

The halide of formula II can be any halide, but the bromide is preferred.

The reaction of 2-methyl-2-pentenal with a halide of formula II is conveniently carried out according to methods which are known per se for Grignard reactions (see, for example, Organikum, Org. chem. Grundpraktikum, reprint 15th Edition, VEB deutscher Verlag der Wissenschaften, Berlin 1977, 617 et seq). Thus, the reaction is conveniently carried out in diethyl ether or a higher alkyl ether or in tetrahydrofuran as the solvent and at temperatures of about 0°–80° C.

The compounds of formula I have particular organoleptic properties which make them especially suitable as odorant substances. The invention is also concerned with their use as odorant substances. Each of the compounds has its own unique characteristics. For example, 4-Methyl-undec-3-en-5-ol (Ia) has a flowery fruity and, at the same time, green odor which is complemented in the bottom by powdery nuances reminiscent of chocolate, while 4,6,8-trimethyl-non-3-en-5-ol (Ig) has above all fruity berry-like and additionally pleasant spicy odor notes. The $C_{4-7}$-alkenyl derivatives possess, for the most part, a surprising additional fatty-butter like odor note.

On the basis of their natural odor notes the compounds of formula I are suitable, in particular, for modifying known compositions, examples of such compositions being:

(a) flowery compositions (e.g. cologne types and the like, essences, soaps and cosmetics) where especially the flowery notes are intensified, and (b) compositions of the chypre and fougère type which, by the addition of compounds of formula I, become "more modern", livelier and, in particular, receive a very pleasant fresh-green aspect (essence types and eau de cologne of the masculine direction).

The compounds I combine with numerous known natural or synthetic ingredients of odorant compositions, whereby the range of the natural ingredients can embrace not only readily-volatile but also semi-volatile and slightly-volatile components and the range of the synthetic ingredients can embrace representatives from almost all classes of substances, as will be evident from the following compilation:

Natural products: Basil oil, tree moss absolute, bergamot oil, cassis bud absolute, cedarwood oil, Cistus labdanum, coriander oil, oak moss absolute, elemi oil, pineneedle oil, galbanum, geranium oil, jasmine absolute and its synthetic substitute, jonquille absolute, lavender oil, mandarin oil, mastix absolute, palmarosa oil, patchouli oil, petitgrain oil Paraguay, sandalwood oil, frankincense, ylang-ylang oil and its synthetic substitute, lemon oil etc.

Alcohols: Citronellol, geraniol, cis-3-hexenol, linalool, Sandela ® (3-isocamphyl-5-cyclohexanol), 2,2,8-trimethyl-7-nonen-3-ol etc.

Aldehydes: α-Amylcinnamaldehyde, cyclamen aldehyde, hydroxycitronellal, 2,6,10-trimethyl-undec-9-en-1-al (Adoxal ™) etc.

Ketones: 3,7,7-Trimethyl-3-[3'-methyl-2'-butenyl]-bicyclo[4,1,0]hepten-4-one, α-ionone, Vertofix ® (acetylated cedarwood oil) etc.

Esters: Amyl salicylate, benzyl acetate, citronellyl acetate, cis-3-hexenyl acetate, 1-methyl-2-sec-butylcyclohexyl acetate, methyl dihydrojasmonate, phenylethyl isobutylate, phenylethyl tiglate, 2,3,6,6-tetramethylcyclohex-2-ene-carboxylic acid ethyl ester, 3,6,6-trimethyl-2-ethyl-cyclohex-2-ene-carboxylic acid ethyl ester etc.

Various: Eugenol, limonene, p-menthane-8-thiol-3-one, 1-methylcyclododecylmethyl ether, γ-undecalactone, musk ambrette, Galaxolid ® (1,3,4,6,7,8-hexahydro-4,6,6,7,8,8-hexamethyl-cyclopenta-γ-2-benzopyran), Musk ketone, Musk 172 TM (12-oxahexadecanolide) etc.

The compounds of formula I can be used in compositions in wide limits which, for example, can extend from 0.1% in the case of detergents to 25% in the case of alcoholic solutions. However, it will be appreciated that these values are not limiting values, since the experienced perfumer can also achieve effects with even lower concentrations or can synthesize novel complexes with even higher concentrations (e.g. with up to 40%). The preferred concentrations range between 0.5% and 20%. The compositions produced with compounds of formula I can be used for all kinds of perfumed consumer goods (eau de cologne, eau de toilette, essences, lotions, creams, shampoos, soaps, salves, powders, toothpastes, mouth washes, deodorants, detergents, tobacco, etc.)

The compounds of formula I can accordingly be used in the production of compositions and, as will be evident from the foregoing compilation, a wide range of known odorant substances can be used. In the production of such compositions, the known odorant substances specified above can be used according to methods which are known to the perfumer such as, for example, according to W. A. Poucher, Perfumes, Cosmetics and Soaps 2, 7th Edition, Chapman and Hall, London, 1974.

ILLUSTRATION OF THE PREFERRED EMBODIMENTS

The following Examples illustrate the present invention:

Example 1

14.30 g (0.59 g-atoms) of magnesium in 100 ml of ether are placed in an apparatus which is customary for Grignard reactions. While stirring and under a protective gas atmosphere (nitrogen) there are subsequently added dropwise 99.0 g (0.60 mol) of 1-bromohexane in 400 ml of absolute ether so that the ether constantly boils slightly after the reaction has started. After completion of the addition, the mixture is held at reflux temperature for a further 30 minutes, then cooled to 10° C. and there is now added dropwise a solution of 49.1 g (0.50 mol) of 2-methyl-2-pentenal in 300 ml of ether during 30 minutes so that the temperature lies permanently between 10° and 25°. In order to complete the reaction, the mixture is held at reflux temperature for a further 1 hour, then the Grignard complex is decomposed with saturated ammonium chloride solution and ice, the supernatant ethereal solution is washed with saturated sodium chloride solution and dried. After evaporation of the solvent, there remain behind 105.3 g of crude product which are fractionally distilled. There are thus obtained 77.8 g (84.4%) of olfactorily good 4-methyl-3-undecen-5-ol of boiling point 66°/0.04 mmHg.

Spectral data: IR: 3340, 2958, 2924, 2858, 1670, 1460, 1378, 1303, 1045, 1002, 854.

MS: 184(M+,7), 169(2), 155(26), 113(5), 99(100), 81(26), 71(15), 55(17), 43(70), 41(18).

Odour: flowery, fruity, green, reminiscent of chocolate.

Example 2

The Grignard reagent, which is obtainable by reacting 3.38 g (0.139 g-atoms) of magnesium in 20 ml of ether and 24.89 g (0.139 mol) of 1-bromoheptane in 80 ml of ether, is reacted with 11.90 g (0.12 mol) of 2-methyl-2-pentenal in 30 ml of ether analogously to Example 1.

The fractional distillation of the crude product (29.5 g) gives 16.3 g (68.5%) of olfactorily good 4-methyl-3-dodecen-5-ol of boiling point 74°/0.04 mmHg.

Spectral data: IR: 3340, 2920, 2850, 1670, 1460, 1375, 1300, 1048, 1010, 852.

MS: 198 (M+, 19), 169(25), 127(7), 109(2), 99(100), 81(17), 69(5), 55(8), 43(20), 41(14).

Odour: green, flowery, fruity.

Example 3

The Grignard reagent, which is obtainable by reacting 3.38 g (0.139 g-atoms) of magnesium in 20 ml of ether and 26.9 g (0.139 mol) of 1-bromooctane in 80 ml of ether, is reacted with 11.80 g (0.12 mol) of 2-methyl-2-penten-1-al in 30 ml of ether analogously to Example 1.

The fractional distillation of the crude product (28.9 g) gives 20.7 g (81.2%) of olfactorily good 4-methyl-3-tridecen-5-ol of boiling point 85°/0.15 mmHg.

Spectral data: IR: 3340, 2920, 2842, 1670, 1458, 1377, 1302, 1112, 1070, 995, 852.

MS: 212(M+,3), 183(12), 141(3), 99(87), 81(24), 71(18), 57(15), 55(22), 43(100), 41(30).

Odour: fruity, green, fatty.

Example 4

The Grignard reagent, which is obtainable by reacting 8.03 g (0.33 g-atoms) of magnesium in 100 ml of ether and 58.18 g (0.35 mol) of 2-bromohexane in 250 ml of ether, is reacted with 28.4 g (0.29 mol) of 2-methyl-2-pentenal in 50 ml of ether analogously to Example 1.

The fractional distillation of the crude product (43.0 g) gives 26.4 g (49.4%) of olfactorily good 4,6-dimethyl-3-decen-5-ol of boiling point 105°/12 mmHg.

Spectral data: IR: 3380, 2958, 2924, 2865, 2855, 1670, 1460, 1378, 1300, 1000, 850.

MS: 184(M+,1), 155(1), 109(1), 99(60), 85(3), 81(15), 71(10), 55(18), 43(100), 41(38).

Odour: green, fatty, flowery, fruity, nuances reminiscent of chocolate.

Example 5

The Grignard reagent, which is obtainable by reacting 3.38 g (0.139 g-atoms) of magnesium in 20 ml of ether and 24.89 g (0.139 mol) of 2-bromoheptane in 80 ml of ether, is reacted with 11.90 g (0.12 mol) of 2-methyl-2-pentenal in 30 ml of ether analogously to Example 1.

The fractional distillation of the crude product (28.7 g) gives 12.1 g (50.9%) of olfactorily good 4,6-dimethyl-3-undecen-5-ol of boiling point 65°/0.04 mmHg.

Spectral data: IR: 3380, 2958, 2920, 2860, 1670, 1458, 1385, 1300, 1000, 850.

MS: 198(M+,6), 169(37), 99(100), 81(5), 71(4), 55(7), 43(17), 41(15).

Odour: green flowery, fruity (berries).

Example 6

The Grignard reagent, which is obtainable by reacting 3.38 g (0.139 g-atoms) of magnesium in 20 ml of ether and 23.0 g (0.139 mol) of 1-bromo-4-methylpentane in 80 ml of ether, is reacted with 11.9 g (0.12 mol) of 2-methyl-2-pentenal in 30 ml of ether analogously to Example 1.

The fractional distillation of the crude product (23.2 g) gives 17.2 g (77.8%) of olfactorily good 2,7-dimethyl-7-decen-6-ol (or 4,9-dimethyl-dec-3-en-5-ol) of boiling point 81°/0.1 mmHg.

Spectral data: IR: 3340, 2950, 2922, 2862, 1670, 1460, 1385, 1365, 1303, 1068, 1045, 1010, 854.

MS: 184(5), 155(13), 109(3), 99(100), 85(11), 81(32), 71(15), 69(17), 55(18), 43(77), 41(20).

Odour: green, fruity, flowery, nuance reminiscent of chocolate.

Example 7

The Grignard reagent, which is obtainable by reacting 19.2 g (0.79 g-atoms) of magnesium in 200 ml of ether and 169.9 g (0.80 mol) of 2-bromo-4-methylpentane in 400 ml of ether, is reacted with 68.0 g (0.69 mol) of 2-methyl-2-pentenal in 200 ml of ether analogously to Example 1.

The fractional distillation of the crude product (137 g) gives 54.0 g (42.5%) of olfactorily good 2,4,6-trimethyl-6-nonen-5-ol (or 4,6,8-trimethyl-non-3-en-5-ol) of boiling point 100°/12 mmHg.

Spectral data: IR: 3400, 2955, 2922, 2863, 1670, 1460, 1384, 1366, 1065, 1005, 960, 853.

MS: 184(M+,<0.2), 109(1), 99(71), 85(5), 81(17), 71(11), 57(7), 55(15), 43(100), 41(22).

Odour: green, fruity (reminiscent of berries), spicy.

Example 8

The Grignard reagent, which is obtainable by reacting 6.60 g (0.27 g-atoms) of magnesium in 30 ml of tetrahydrofuran and 28.50 g (0.27 mol) of 3-methyl-3-buten-1-yl chloride in 120 ml of tetrahydrofuran, is reacted with 22.90 g (0.23 mol) of 2-methyl-2-pentenal in 40 ml of tetrahydrofuran analogous to Example 1.

The fractional distillation of the crude product (46.6 g) gives 24.1 g (62.3%) of olfactorily good 2,6-dimethyl-1,6-nonadien-5-ol of boiling point 62°/0.03 mmHg.

Spectral data: IR: 3340, 2065, 2955, 2922, 2860, 1650, 1440, 1370, 1300, 1060, 1008, 882, 855.

MS: 168(M+,2), 150(49), 139(68), 121(15), 112(82), 99(100), 81(40), 69(31), 55(30), 43(50).

Odour: flowery, fruity, leaf-like, slightly bitter, nuances reminiscent of cocoa.

Example 9

The Grignard reagent, which is obtainable by reacting 3.38 g (0.139 g-atoms) of magnesium in 20 ml of tetrahydrofuran and 16.5 g (0.139 mol) of cis-3-hexenyl chloride in 70 ml of tetrahydrofuran, is reacted with 11.8 g (0.12 mol) of 2-methyl-2-pentenal in 20 ml of tetrahydrofuran analogously to Example 1.

The fractional distillation of the crude product (33.1 g) gives 12.8 g (58.5%) of olfactorily good 4-methyl-3,8(Z)-undecadien-5-ol of boiling point 58°/0.03 mmHg.

Spectral data: IR: 3340, 3000, 2955, 2922, 2862, 1660, 1452, 1302, 1060, 1000, 855, 720.

MS: 182(M+,2), 153(13), 100(18), 99(37), 81(28), 71(20), 69(28), 55(28), 43(100), 41(45).

Odour: green, buttery, flowery.

Example 10

The Grignard reagent, which is obtainable by reacting 7.10 g (0.29 g-atoms) of magnesium in 50 ml of ether and 43.60 g (0.29 mol) of 4-penten-1-yl bromide in 200 ml of ether, is reacted with 24.50 g (0.25 mol) of 2-methyl-2-pentenal in 50 ml of ether analogously to Example 1.

The fractional distillation of the crude product (43.7 g) gives 29.8 g (70.8%) of olfactorily good 4-methyl-3,9-decadien-5-ol of boiling point 101°/12 mmHg.

Spectral data: IR: 3340, 3075, 2960, 2925, 2860, 1645, 1460, 1304, 1060, 1015, 990, 908, 853.

MS: 168(M+,3), 139(30), 125(8), 99(100), 81(37), 71(17), 69(31), 55(28), 43(92), 41(31).

Odour: green, metallic, fatty.

Example 11

The Grignard reagent, which is obtainable by reacting 6.60 g (0.27 g-atoms) of magnesium in 50 ml of ether and 45.00 g (0.28 mol) of 4-methyl-3-penten-1-yl bromide in 150 ml of ether, is reacted with 23.65 g (0.24 mol) of 2-methyl-2-pentenal in 70 ml of ether analogously to Example 1.

The fractional distillation of the crude product (50.0 g) gives 31.7 g (72.4%) of olfactorily good 2,7-dimethyl-2,7-decadien-6-ol (or 4,9-dimethyl-3,8-decadien-5-ol) of boiling point 115°/12 mmHg.

Spectral data: IR: 3350, 2960, 2922, 2865, 2855, 1670, 1450, 1375, 1105, 1052, 1005, 855, 829.

MS: 182(M+,20), 153(53), 135(16), 125(19, 121(14), 99(55), 97(42), 93(25), 83(37), 81(50), 71(35), 69(60), 55(47), 43(100), 41(62).

Odour: fatty, aldehydic, green flowery.

Example 12

0.89 g (0.037 g-atoms) of magnesium in 5 ml of absolute ether are reacted at the boiling temperature of the ether with a solution of 6.6 g (0.037 mol) of 5-methyl-4-hexenyl bromide in 20 ml of absolute ether analogously to the preceding Examples. After completion of the addition, the mixture is held at reflux temperature for a further 30 minutes. Subsequently, 3.0 g (0.03 mol) of 2-methyl-2-pentenal in 5 ml of absolute ether are added dropwise at room temperature during 30 minutes so that the ether again begins to boil. After refluxing for a further hour, the mixture is cooled, decomposed with ice and saturated ammonium chloride solution and worked-up. There are thus obtained 2.9 g of 4,10-dimethyl-3,9-undecadien-5-ol of boiling point 110°/0.06 mmHg, $n_D^{20} = 1.4705$.

Spectral data: IR: 3360, 1670, 1454, 1380, 1072, 1024, 1000, 864 cm$^{-1}$.

MS: 196(6,M+), 167(13), 149(5), 125(26), 99(35), 96(25), 82(100), 81(52), 69(31), 55(37), 43(71).

Odour: fruity (melon), flowery (cyclamen), fresh, green.

Example 13

Green-flowery perfumery base:

| | Parts by weight |
|---|---|
| Hydroxycitronellal | 250 |
| Methyl dihydrojasmonate | 250 |
| Dipropylene glycol | 200 |
| Bergamot oil | 100 |
| Citronellol | 50 |
| p-Menthane-8-thiol-3-one | 10 |
| Mandarin oil | 10 |
| Galbanum oil | 10 |
| Jasmine synthetic | 10 |
| Palmarosa oil | 10 |
| Mastix absolute | 5 |
| Geranium oil | 5 |
| Cyclamen aldehyde | 5 |
| Coriander oil | 5 |
| Phenylethyl isobutyrate | 5 |
| Cis-hexenol (10% in dipropylene glycol) | 5 |
| Basil oil | 3 |
| Cassis bud oil absolute | 2 |
| | 935 |

The addition of 65 parts of 4-methyl-3-undecen-5-ol underlines the flowery side of the original composition. A previously unrecognizable muguet character results.

By adding 65 parts of 4-methyl-3,8(Z)-undecadien-5-ol the odour character of the composition is altered in an impressive manner. A fruity (berry-like), spicy impression results, and simultaneously an eau de cologne effect is produced by complexing with the citrus ingredients of the composition.

Example 14

General flowery base:

| | Parts by weight |
|---|---|
| Dipropylene glycol | 200 |
| Limonene | 150 |
| α-Ionone | 60 |
| Citronellol | 50 |
| Linalool | 50 |
| Vertofix coeur | 50 |
| Galaxolide ® 50 (1,3,4,6,7,8-hexahydro-4,6,6,7,8,8-hexamethyl-cyclopenta-γ-2-benzopyran | 30 |
| Benzyl acetate | 30 |
| 2-Ethyl-3,6,6-trimethyl-2-cyclohexen-1-yl-carboxylic acid ethyl ester | 30 |
| Jasmine synthetic | 20 |
| Musk ketone | 20 |
| Phenylethyl tiglate | 20 |
| 2,2,8-Trimethyl-7-nonen-3-ol | 15 |
| Frankincense (50% in dipropylene glycol) | 15 |
| Citronellyl acetate | 10 |
| Hexenyl acetate (10% in dipropylene glycol) | 10 |
| Ylang-ylang oil | 10 |
| Ylang-ylang synthetic | 10 |
| Lemon oil | 10 |
| Undecalactone | 10 |
| Cyclamen aldehyde | 5 |
| Galbanum oil | 5 |
| Sandalwood oil | 5 |
| Jonquille absolute (10% in dipropylene glycol) | 5 |
| Ciste labdanum oil | 5 |
| Adoxal (10% in dipropylene glycol) | 5 |
| | 830 |

170 parts of 4-methyl-3-dodecen-5-ol underline the sandal-flowery complex in the foregoing composition and therewith intensify the desired impression of this composition.

On the other hand, 170 parts of 4,6,8-trimethyl-3-nonen-5-ol produce a most amazing effect in the base; in spite of the very green character of this substance there results in the base a very pleasant berry-like, also cosmetic green-flowery odour complex which is well suited for soaps.

The addition of 2,6-dimethyl-1,6-nonadien-5-ol emphasizes the green-flowery aspect, i.e. the novel compound complexes with other components (e.g. with galbanum) of the original base.

Example 15

Perfumery (chypre) base:

| | Parts by weight |
|---|---|
| 1-Methyl-1-methoxy-cyclododecane | 200 |
| Bergamot oil | 150 |
| Hydroxycitronellal | 100 |
| Citronellol | 80 |
| Petitgrain oil | 60 |
| 12-Oxa-hexadecanolide | 60 |
| Coriander oil | 40 |
| Galbanum oil | 40 |
| Cedarwood oil | 40 |
| Patchouli oil | 40 |
| Lemon oil | 40 |
| Elemi oil | 10 |
| Oak moss absolute | 10 |
| Pine-needle oil | 125 |
| | 995 |

The addition of 5 parts of 4-methyl-3-undecen-5-ol freshens the green and herb-like aspects of this composition.

On the other hand, 5 parts of 4,6,8-trimethyl-3-nonen-5-ol produce in this base a much greater diffusion; the novel base becomes much fresher, greener and also more spicy, so that it is very suitable for a modern man's cologne. The effect is similar with that produced with 4-methyl-3-undecen-5-ol, but is substantially more pronounced.

Example 16

Perfumery base in the direction of fougère:

| | Parts by weight |
|---|---|
| Lavender oil | 200 |
| Amyl salicylate | 180 |
| Tree moss (50% in dipropylene glycol) | 100 |
| Citronellol | 100 |
| Geraniol | 80 |
| Musk ambrette | 80 |
| Bergamot oil | 80 |
| α-Ionone | 80 |
| α-Amylcinnamaldehyde | 25 |
| Eugenol | 25 |
| Metambrate ™ Giv (1-acetoxy-1-methyl-2-sec.butyl-cyclohexane) | 20 |
| | 970 |

If 30 parts of 4-methyl-3-undecen-5-ol are added to this fougère composition, then it becomes much fresher and greener; it receives more volume (substantially intensified diffusion) and thereby is much stronger than the composition without the addition.

4,6,8-Trimethyl-3-nonen-5-ol underlines, in particular, the herb-like note. The addition of this compound thus confers more life to the fougère composition.

Example 17

Perfumery composition of the cologne type:

| | Parts by weight |
|---|---|
| Dipropylene glycol | 450 |
| Myrascone ™ Giv (2-ethyl-3,6,6-trimethyl-cyclohexen-1-yl-carboxylic acid ethyl ester) | 80 |
| Galaxolide ® 50 (IFF) | 60 |
| Hydroxycitronellal | 60 |
| Madrox ™ Giv (1-methyl-1-methoxy-cyclododecane) | 60 |
| Sandela | 60 |
| Bergamot oil | 60 |
| Pine-needle oil | 30 |
| Musk ketone | 30 |
| Givescone ™ Giv | 30 |
| 3,7,7-Trimethyl-3-[3'-methyl-2'-butenyl]-bicyclo[4.1.0]heptan-4-one (isomer mixture) | 20 |
| Petitgrain oil | 15 |
| p-Menthane-8-thiol-3-one | 5 |
| Tree moss absolute | 5 |
| | 965 |

An addition of 35 parts of 4-methyl-3-undecen-5-ol confers to this eau de cologne type composition a flowery nuance and therewith underlines its feminine character.

On the other hand, by adding 35 parts of 2,6-dimethyl-1,6-nonadien-5-ol the cologne base subsequently becomes much more spicy and herb-like. It is very much fresher and livelier and now moves much more in the direction of man's eau de cologne.

We claim:

1. A compound of the formula

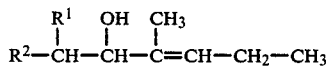

wherein:
R¹ is selected from the group consisting of hydrogen and methyl;
R² is selected from the group consisting of normal or terminally singly branched alkyl or alkenyl groups having four to seven carbon atoms provided that:
 (i) when R¹ is hydrogen the alkyl group must have at least five carbon atoms, and
 (ii) when R¹ is methyl, R² is an alkyl group.

2. A compound according to claim 1 selected from the group consisting of 4-methyl-dodec-3-en-5-ol, 4-methyl-tridec-3-en-5-ol, 4,6-dimethyl-undec-3-en-5-ol, 4,7,8-trimethyl-non-3-en-5-ol, 4-methyl-3,9-decadien-5-ol, 4-methyl-3,8-undecadien-5-ol, 4,9-dimethyl-3,8-decadien-5-ol and 4,10-dimethyl-3,9-undecadien-5-ol.

3. A compound of claim 1 identified as 4-methyl-undec-3-en-5-ol.

4. A compound of claim 1 identified as 4,6-dimethyl-dec-3-en-5-ol.

5. A compound of claim 1 identified as 4,9-dimethyl-dec-3-en-5-ol.

6. A compound of claim 1 identified as 4,6,8-trimethyl-non-3-en-5-ol.

7. A compound of claim 1 identified as 2,6-dimethyl-1,6-nonadien-5-ol.

8. An odorant composition comprising an olfactorily effective amount of a compound of the formula:

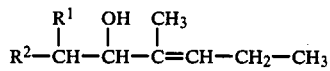

wherein:
R¹ is selected from the group consisting of hydrogen and methyl;
R² is selected from the group consisting of normal or terminally singly branched alkyl or alkenyl groups having four to seven carbon atoms provided that:
 (i) when R¹ is hydrogen the alkyl group must have at least five carbon atoms, and
 (ii) when R¹ is methyl, R² is an alkyl group and, at least one other olfactory agent.

9. A composition according to claim 8 wherein there is present at least one of the compounds selected from the group consisting of 4-methyl-dodec-3-en-5-ol, 4-methyl-tridec-3-en-5-ol, 4,6-dimethyl-undec-3-en-5-ol, 4,7,8-trimethyl-non-3-en-5-ol, 4-methyl-3,9-decadien-5-ol, 4-methyl-3,8-undecadien-5-ol, 4,9-dimethyl-3,8-decadien-5-ol and 4,10-dimethyl-3,9-undecadien-5-ol.

10. A composition according to claim 8 containing 4-methyl-undec-3-en-5-ol.

11. A composition according to claim 8 containing 4,6-dimethyl-dec-3-en-5-ol.

12. A composition according to claim 8 containing 4,9-dimethyl-dec-3-en-5-ol.

13. A composition according to claim 8 containing 4,6,8-trimethyl-non-3-en-5-ol.

14. A composition according to claim 8 containing 2,6-dimethyl-1,6-nonadien-5-ol.

15. A method for improving the olfactory properties of odorant compositions which comprises adding thereto an effective amount of a compound of the formula:

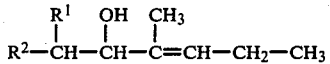

wherein:
R¹ is selected from the group consisting of hydrogen and methyl;
R² is selected from the group consisting of normal or terminally singly branched alkyl or alkenyl groups having four to seven carbon atoms provided that:
 (i) when R¹ is hydrogen the alkyl group must have at least five carbon atoms, and
 (ii) when R¹ is methyl, R² is an alkyl group.

16. A method according to claim 15 wherein there is added at least one of the compounds selected from the group consisting of 4-methyl-dodec-3-en-5-ol, 4-methyl-tridec-3-en-5-ol, 4,6-dimethyl-undec-3-en-5-ol, 4,7,8-trimethyl-non-3-en-5-ol, 4-methyl-3,9-decadien-5-ol, 4-methyl-3,8-undecadien-5-ol, 4,9-dimethyl-3,8-decadien-5-ol and 4,10-dimethyl-3,9-undecadien-5-ol.

17. A method according to claim 15 wherein there is added 4-methyl-undec-3-en-5-ol.

18. A method according to claim 15 wherein there is added 4,6-dimethyl-dec-3-en-5-ol.

19. A method according to claim 15 wherein there is added 4,9-dimethyl-dec-3-en-5-ol.

20. A method according to claim 15 wherein there is added 4,6,8-trimethyl-non-3-en-5-ol.

21. A method according to claim 15 wherein there is added 2,6-dimethyl-1,6-nonadien-5-ol.

* * * * *

UNITED STATES PATENT AND TRADEMARK OFFICE
CERTIFICATE OF CORRECTION

PATENT NO. : 4,572,795

DATED : February 25, 1986

INVENTOR(S) : Roman Kaiser et al.

It is certified that error appears in the above-identified patent and that said Letters Patent is hereby corrected as shown below:

The portion of the term of this patent subsequent to November 13, 2001 has been disclaimed.

Signed and Sealed this

Third Day of July, 1990

*Attest:*

HARRY F. MANBECK, JR.

*Attesting Officer*      *Commissioner of Patents and Trademarks*